United States Patent
Arnovick

(10) Patent No.: US 12,076,465 B2
(45) Date of Patent: Sep. 3, 2024

(54) ROTARY SEPARATION APPARATUS AND PROCESS OF USE

(71) Applicants: The Original Resinator, LLC, Graton, CA (US); Travis J. Arnovick, Graton, CA (US)

(72) Inventor: Travis Jeremy Arnovick, Graton, CA (US)

(73) Assignee: The Original Resinator, LLC, Graton, CA (US)

( * ) Notice: Subject to any disclaimer, the term of this patent is extended or adjusted under 35 U.S.C. 154(b) by 0 days.

(21) Appl. No.: 17/782,662

(22) PCT Filed: Dec. 7, 2020

(86) PCT No.: PCT/US2020/063631
§ 371 (c)(1),
(2) Date: Jun. 5, 2022

(87) PCT Pub. No.: WO2021/113826
PCT Pub. Date: Jun. 10, 2021

(65) Prior Publication Data
US 2023/0009441 A1    Jan. 12, 2023

Related U.S. Application Data

(60) Provisional application No. 62/943,925, filed on Dec. 5, 2019.

(51) Int. Cl.
*B07B 1/22* (2006.01)
*A61L 9/03* (2006.01)
(Continued)

(52) U.S. Cl.
CPC .............. *A61L 9/127* (2013.01); *A61L 9/037* (2013.01); *B07B 1/22* (2013.01); *B07B 1/42* (2013.01);
(Continued)

(58) Field of Classification Search
CPC .... B07B 1/08; B07B 1/14; B07B 1/18; B07B 1/22; B07B 1/42; B07B 4/06; B07B 7/083
(Continued)

(56) References Cited

U.S. PATENT DOCUMENTS 3,385,478 A    5/1968  Miller et al.
5,556,202 A *  9/1996  Dorn .................... B01F 35/421
                                                    366/220
(Continued)

FOREIGN PATENT DOCUMENTS

CN    109433580 A  *  3/2019
CN    110152973 A  *  8/2019
(Continued)

OTHER PUBLICATIONS

International Search Report and Written Opinion on Patentability in PCT/US20/63631, Inventor:Arnovick, T. dated Apr. 12, 2021.
International Search Report & Written Opinion for corresponding PCT/US20/63631 (dated Apr. 12, 2021), 12 pages.

*Primary Examiner* — Gene O Crawford
*Assistant Examiner* — Muhammad Awais
(74) *Attorney, Agent, or Firm* — Incubate IP; Randy R. Micheletti

(57) ABSTRACT

A rotary separation devise deploys a drum with mesh like opening on the cylindrical surfaces and a removable cover or cap for filling in an upright position and removal of product or spent matter in an inverted position. When the drum is loaded with material, and the cover closed, it is rotatable to a horizontal position, and disposed in an outer container. The drum is rotated in the horizontal position to initiate the separation process. The outer container may be formed by the mating engagement at a common rim of an upper and lower vessel that form the sealed container.

12 Claims, 16 Drawing Sheets

(51) Int. Cl.
  *A61L 9/12* (2006.01)
  *B07B 1/42* (2006.01)
  *B27K 5/00* (2006.01)
  *B27K 5/06* (2006.01)
  *B27K 9/00* (2006.01)
  *C11C 5/00* (2006.01)

(52) U.S. Cl.
  CPC .............. *B27K 5/007* (2013.01); *B27K 5/065* (2013.01); *B27K 9/002* (2013.01); *B27K 2240/10* (2013.01); *C11C 5/006* (2013.01)

(58) Field of Classification Search
  USPC ......................................................... 209/284
  See application file for complete search history.

(56) References Cited

U.S. PATENT DOCUMENTS

| | | | |
|---|---|---|---|
| 5,628,912 | A | 5/1997 | Nesseth |
| 2005/0056583 | A1 | 3/2005 | Diemer et al. |
| 2007/0234690 | A1 | 10/2007 | Ryan |
| 2018/0008656 | A1* | 1/2018 | Watts .................. A23L 3/44 |
| 2019/0083558 | A1 | 3/2019 | Watts et al. |

FOREIGN PATENT DOCUMENTS

| | | |
|---|---|---|
| CN | 110369262 A * | 10/2019 |
| EP | 0832675 A2 * | 4/1998 |

* cited by examiner

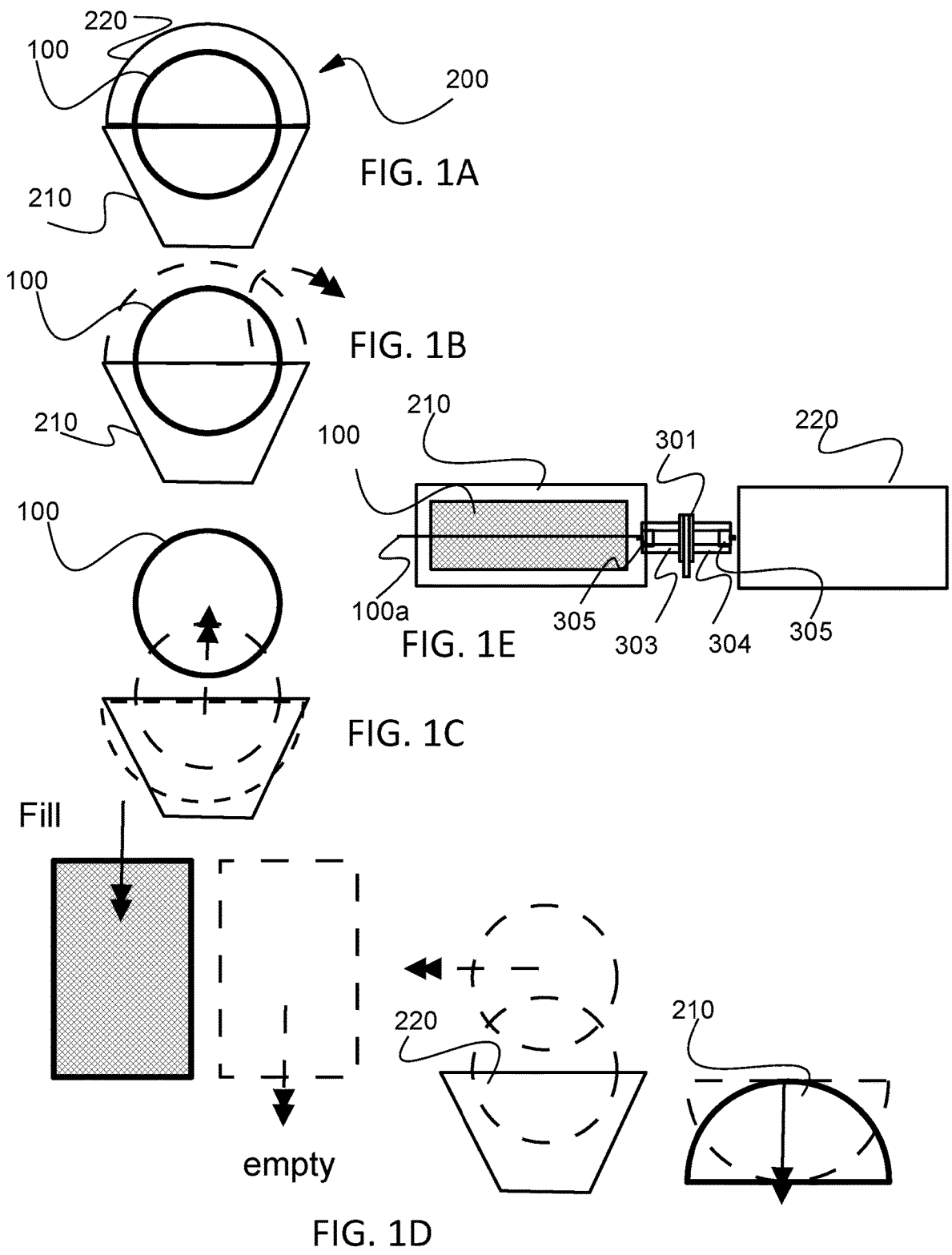

Fill empty

Invert lower vessel

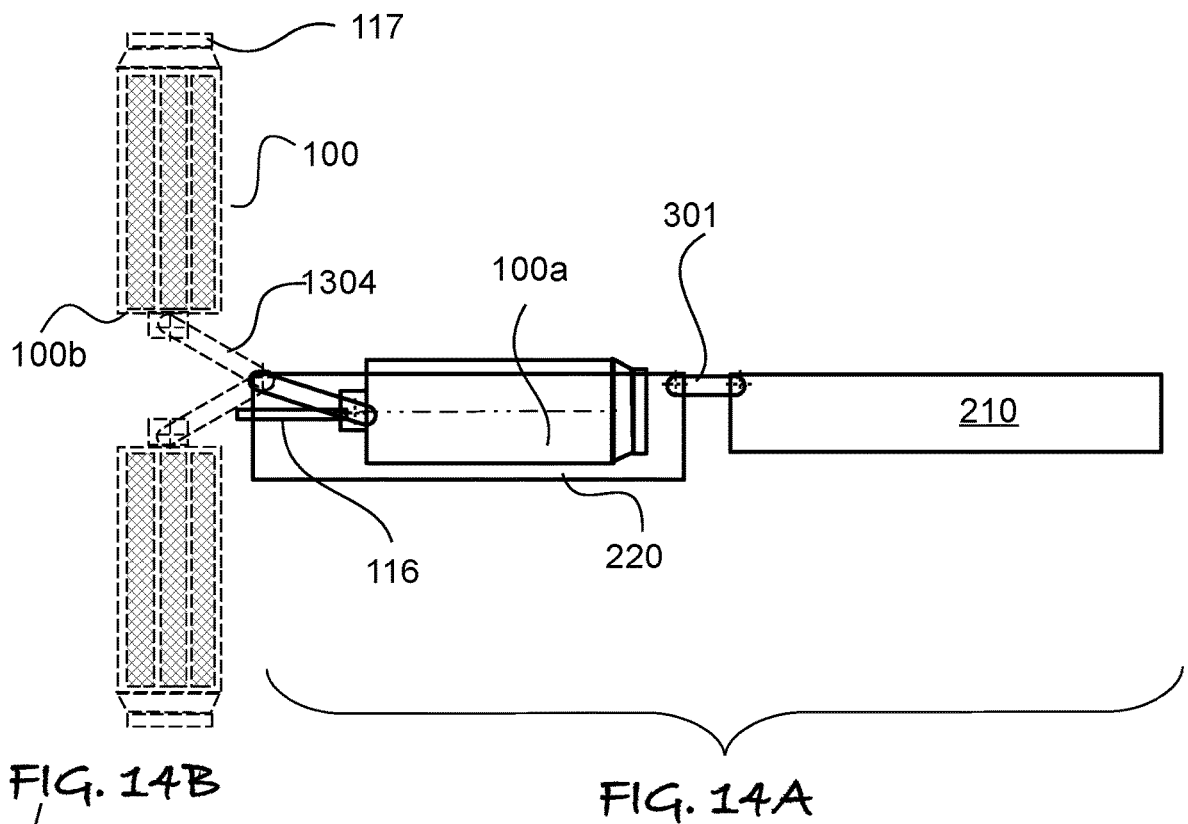
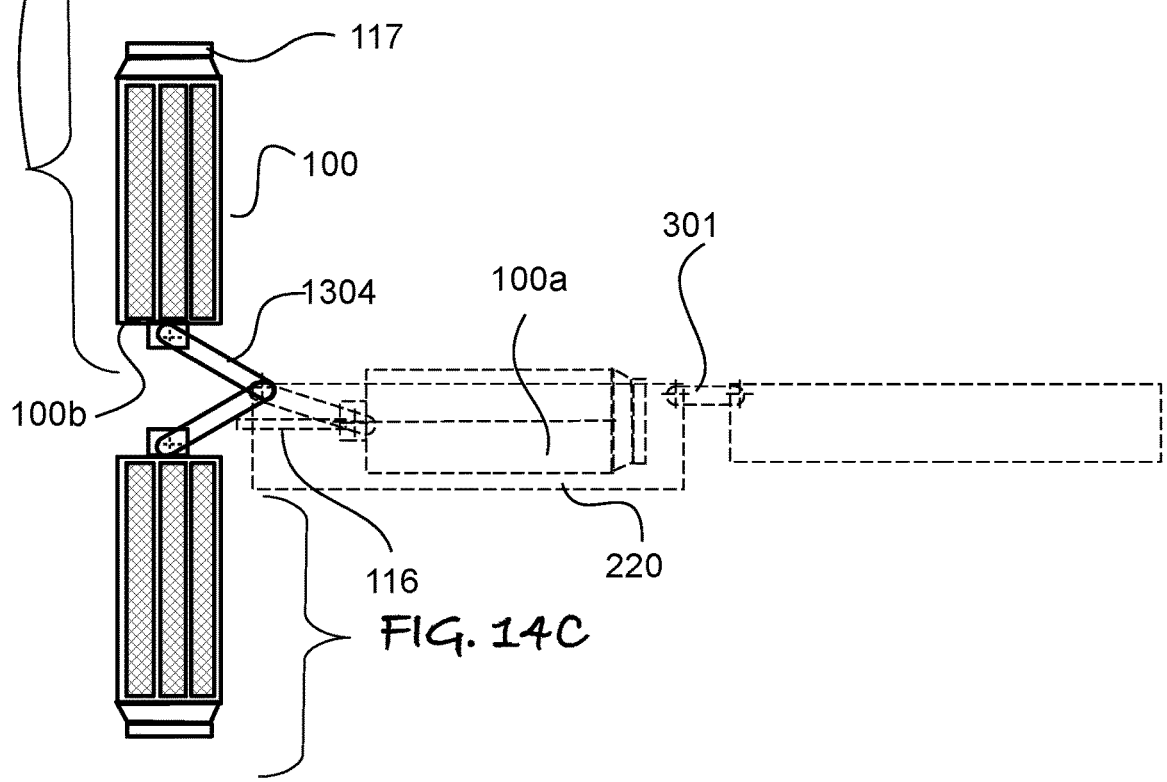
FIG. 14B
FIG. 14A
FIG. 14C

ROTARY SEPARATION APPARATUS AND PROCESS OF USE

CROSS REFERENCE TO RELATED APPLICATIONS

The present application claims the benefit of priority to the U.S. Provisional Patent Application that was filed on Dec. 5, 2019, having application No. 62/943,925, and is incorporated herein by reference. The present application also claims the benefit of priority to the International/PCT application that was filed on Dec. 7, 2020, having International Application No. PCT/US20/63631 and is incorporated herein by reference.

BACKGROUND OF INVENTION

The field of inventions is processing plant and botanical materials to extract components and separating the components by size, and more particularly a rotary separation apparatus that contains the plant or botanic material.

Rotary separation machine deploy an outer chamber or container that forms an outer bound space for collecting material that exits through screens, perforation or mesh that forms an outer portion of an inner bound chamber that is rotated to agitate and tumbled the plant or botanical materials. The tumbling, agitation and shear that may be provided to the screen, mesh perforation and/or other contents and conditions may further breakdown the plant matter to isolate more desired components that can then be separated by size from desired plant matter. The rotation process will continuously expose the contents of the inner bound container to the perforated covering so matter smaller than the holes or perforation can pass through to be collected in the outer chamber. Depending on the plant or botanical matter and the intended purpose, it may be desirable to utilize the material that is in the inner bound chamber or that which exits it, as well as both these materials, which can then undergo different process or uses.

The inventor has discovered various improvements in equipment and processes to process plant and botanical matter that are disclosed in the commonly owned U.S. Pat. No. 10,512,938B2 which issued Dec. 24, 2019, and U.S. Pat. No. 10,507,223B2 which issued Dec. 17, 2019, which are incorporated herein by reference.

The productivity, capacity and cost effectiveness of these processes can be improved as disclosed in the apparatus and methods disclosed below.

The above and other objects, effects, features, and advantages of the present invention will become more apparent from the following description of the embodiments thereof taken in conjunction with the accompanying drawings

SUMMARY OF INVENTION

In the present invention, the first object is achieved by providing a rotary separation apparatus that comprises a drum having a generally cylindrical shape with a primary axis coincident with the principal axis of the cylinder, in which the drum has lateral surface with a plurality of perforations and a base of the cylinder that is opposed to an upper of the cylinder, a container that forms an enclosed space around the drum when the drum is disposed with the principal axis in a horizontal orientation, one of more actuators that are operative modulate the orientation of the principal axis of the cylinder from between an upright and inverted vertical orientation and dispose the drum horizontally in the container, a means to rotate the drum about the principal axis when the drum is disposed horizontally within the container.

A second aspect of the invention is characterized by such a rotary separation apparatus in which the drum has a removable cap that closes an opening in the upper end of the cylinder.

Another aspect of the invention is characterized by any such rotary separation apparatus in which the container forms the enclosed space when an upper and lower vessel are brought into mutual engagement at a rim of the upper vessel to a rim of the lower vessel.

Another aspect of the invention is characterized by any such rotary separation apparatus in which the lower vessel is capable of being inverted from an upright horizontal orientation to a downward facing horizontal orientation by the one or more actuators to empty the contents thereof via the opening in the upper end of the cylinder.

Another aspect of the invention is characterized by any such rotary separation apparatus when the one of more actuators are operative to modulate the orientation of drum from being disposed with the principal axis of the cylinder horizontally within the container to vertically outside the container by rotating the upper vessel away from the lower vessel to dispose both the upper vessel and the lower vessel in an upward facing orientation and then rotating the drum to dispose the principal axis of the cylinder vertically.

Another aspect of the invention is characterized by any such rotary separation apparatus wherein the one of more actuators includes a first motor and second motor in which the first motor is operative to rotate the upper vessel away from the lower vessel and the drum is rotated between the vertical and horizontal orientation of the principal axis of the cylinder by the second motor the coupled to a support frame that is external to common housing that contains the first motor to rotate the common housing at least 60 degrees.

Another aspect of the invention is characterized by any such rotary separation apparatus wherein the means to rotate the drum about the principal axis when the drum is disposed horizontally within the container is a primary motor coupled to the common housing to rotate a shaft that extends through the common housing to connect to the base of the cylinder in which the shaft extends in the direction of the principal axis of the cylinder.

Another aspect of the invention is characterized by any such rotary separation apparatus wherein the one of more actuators includes a third motor that is connected to the support frame and the second motor is mounted at a distal end of a primary arm and the proximal end of the primary arm is connected to the third motor in which the third motor is operative to rotate the primary arm from a horizontal to a vertical orientation before the one of more actuators are operative modulate the orientation of the principal axis of the cylinder from an upright to an inverted vertical orientation Another aspect of the invention is characterized by any such rotary separation apparatus wherein the container is sealed by a portal with a cover that supports an axle that is coupled to rotate the drum about the principle axis and the apparatus is configured to remove the drum via the portal and disposes a motor on the opposite side of the cover.

Another aspect of the invention is characterized by any such rotary separation apparatus in which the container comprises in a lower portion a drawer disposed to collect matter that exits the drum via the plurality of perforation in which the drawer is configured translate away from the lower portion to provide access to the collected matter.

Another aspect of the invention is characterized by any such rotary separation apparatus wherein the one or more actuators is operative to remove the container laterally via a side portal such that it translates in the direction of the principal axis.

Another aspect of the invention is characterized by any such rotary separation apparatus wherein the upper and lower vessel are configured to be separated to remove the drum by a rotary joint that is spaced apart from the rim of both the upper and lower vessel such that the inverted upper vessel is spaced apart from the lower vessel when the drum is removed from the opened container.

Another aspect of the invention is characterized by a system for processing materials in a rotary separation apparatus, in which the rotary separation apparatus comprises a drum having a generally cylindrical shape with a primary axis coincident with the principal axis of the cylinder, in which the drum has lateral surface with a plurality of perforations, a container that forms an enclosed space around the drum when the drum is disposed with the principal axis in a horizontal orientation, one of more actuators to invert the drum when out of the container and dispose the drum horizontally in the container, a means to rotate the drum about the principal axis when the drum is disposed horizontally within the container, at least a first conveyor belt configured to transport material to an opening in an upper end of the cylinder when the drum is oriented with the principal axis in the vertical orientation.

Another aspect of the invention is characterized by such a system for processing materials in a rotary separation apparatus in which the container that forms the enclosed space around the drum comprises an upper and lower vessel in which the upper vessel is disposed over and in sealed engagement to the lower vessel when the drum is disposed with the principal axis of the cylinder horizontal when within the container and further comprising a second conveyor belt disposed to receive material from the lower vessel when upper vessel is removed from the lower vessel and lower vessel is inverted from an upright horizontal orientation to a downward facing horizontal orientation.

Another aspect of the invention is characterized by any such system for processing materials in a rotary separation apparatus wherein the first conveyor belt is operative to lift material from a hopper to at least the height of the open end of the container such that material on exiting an end of the conveyor distal from the hopper falls into the container.

Another aspect of the invention is characterized by a process for treating materials, the process comprising the steps of providing a drum having perforation on lateral surfaces and an upper surface with a closable opening, the drum being defined by a cylindrical axis that is disposed orthogonal to the upper surface and a base that is disposed opposite the upper surface and is also disposed parallel to the lateral surfaces, providing a container to surround the drum when disposed in an orientation when the cylindrical axis is closer to a horizontal orientation than a vertical orientation, charging the drum with material to be processed via the opening when the drum is outside the container and the opening is disposed above the base, closing the opening, disposing the drum with the cylindrical axis is closer to a horizontal orientation than a vertical orientation, rotating the drum within the container, removing the drum from the container, orienting the drum with the base disposed above the opening to discharge material from the container.

Another aspect of the invention is characterized by such a process for treating materials further comprising a step of removing material that traversed the drum lateral surfaces via the perforations from the container.

Another aspect of the invention is characterized by any such process for treating materials where the material that traversed the drum lateral surfaces via the perforations is removed from the container by one of a drawer or shoot that translates or pivot away from a lower portion of the container.

Another aspect of the invention is characterized by any such process for treating materials where the material that traversed the drum lateral surfaces via the perforations is removed from the container by opening the container along a seam that separates connected portions and tilting at least on connected portion by rotation to pour out the material.

Another aspect of the invention is characterized by any such process for treating materials wherein the container is separated at a lateral seam to dispose a lower vessel under the drum that collects the material separated by the drum.

Another aspect of the invention is characterized by any such process for treating materials wherein the step of removing the drum from the container occurs after the step of orienting the drum with the base disposed above the opening to discharge material from the container.

In other aspects of the invention, the upper and lower vessels are configurable to use different separation processes and media. A resulting product may be retained in the drum by the mesh or pass through the mesh to enter the lower vessel. This product can be removed from a vessel or drum by inverted it after the vessels are separated from the drum. In some embodiments, the drum, upper and lower vessel are manipulated by a common multi-axis actuator that is capable of both separating the drum from each vessel and the selective orientation of each component as necessary for the removal of the resulting product, as well as then refilling the drum to repeat the separation process. The common multi-axis actuator may also rotate the drum in the horizontal position. The separation process may be semi-continuous via the rapid repetition of batch operations in which the spacing and orientation of the vessels and the drum before and after the separation process permit feeding of material, product and spent matter by different conveyor belts.

The above and other objects, effects, features, and advantages of the present invention will become more apparent from the following description of the embodiments thereof taken in conjunction with the accompanying drawings.

BRIEF DESCRIPTION OF DRAWINGS

FIG. 1A to 1E is a schematic diagram to illustrate a sequence of steps in an embodiment of the apparatus and method, in which FIG. 1A-D are schematic side elevations and FIG. 1E is a top plan view.

FIG. 2A to 2D is a schematic diagram to illustrate a related sequence of steps in an embodiment of the apparatus and method, in which FIG. 1A-D are schematic side elevations

FIG. 14 is a schematic side elevation view of the embodiment of the apparatus in FIG. 13 illustrating alternative positions and orientations of the drum in and outside of the container.

DETAILED DESCRIPTION

Figure 2A:
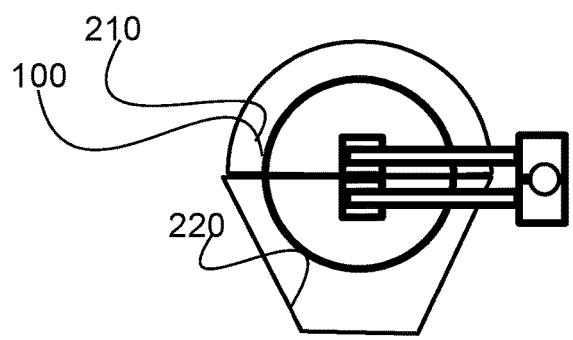

Referring to FIGS. 1 through 16, wherein like reference numerals refer to like components in the various views, there is illustrated therein a new and improved Rotary Separation Apparatus, generally denominated 1000 herein.

In accordance with the present invention the Rotary Separation Apparatus 1000 comprises a drum 100 having a generally cylindrical shape with a primary axis 100a coincident with the principal axis of the cylinder, in which the drum 100 has lateral surface 110 with a plurality of perforations 111. A container 200 forms an enclosed space around the drum 100 when the drum 100 is disposed with the principal axis 100a in a generally horizontal orientation. One or more actuators 300 may invert the drum 100 when out of the container 200 to dispose the drum 100 generally vertically and dispose the drum 100 horizontally within the container 200. The rotary separation apparatus 1000 also comprises a means to rotate the drum 100 when the drum 100 is disposed horizontally within the container 200.

It should be understood that the terms horizontal and vertical are not limited to strictly parallel and perpendicular to the ground but may embrace variation of at least 5-30 degrees and still provide the intended functions and resulting benefits of the process for treating materials 1600. Process 1600 may comprise the steps of providing a drum 100 having perforation 111 on lateral surfaces and an upper surface with a closable opening, the drum being defined by a cylindrical axis that is disposed orthogonal to the upper surface and a base that is disposed opposite the upper surface and is also disposed parallel to the lateral surfaces (step 1605), providing a container 200 to surround the drum 100 when disposed in an orientation when the cylindrical axis is closer to a horizontal orientation than a vertical orientation (step 1610), charging the drum 100 with material to be processed via the opening when the drum is outside the container and the opening is disposed above the base (step 1615), closing the opening (step 1620), disposing the drum 100 with the cylindrical axis 100a is closer to a horizontal orientation than a vertical orientation (step 1625), rotating the drum 100 within the container 200 (step 1630), removing the drum 100 from the container 200, orienting the drum 100 with the base disposed above the opening to discharge material from the drum (step 1635).

The perforation 111 may be provided by forming the lateral surface from 110 from a plurality of panel that are assembled into a frame work, each panel being formed of rigid sides that form a supporting frame, with a screen, mesh or perforated plate(s) extending across the frame. Alternatively, the perforation 110 may be provided by wrapping a flexible screen or mesh around the entire lateral surface 110, or across each panel. The lateral surface 110 can be continuously curved, curvilinear or a faceted, such as a multi-sided polygon, and combinations thereof and the like.

In preferred embodiments, the container 200 is formed of an upper 210 and a lower 220 vessel that mate at a common junction of their rims 211 and 221, respectively. A gasket 215 may be disposed on one of the rims 211 or 221 such that a fluid tight seal is formed when the one or more actuator(s) 300 is deployed to urge the rims 221 and 211 into contact.

The vessels 210 and 220 may have any shape and are preferably shapes to contain a fluid when the rim 118 is disposed above the interior of the container 200 and the upper 210 and lower vessel 220. However, to reduce the size and facilitate separating the vessels 210 and 220, it is preferred that are shaped generally like the drum 100 but larger, leaving a space to provide media, such as a freezing agent, that aids in the separation process, as well as to collect the components or product that exits through the perforations 111. It may be desirable to provide a deeper lower vessel 220 to provide more capacity for separated matter.

In some processes, the desired product is retained in the drum 100, while a less valuable or waste product passes through the perforations 111 when the drum 100 is rotated about the primary axis 100a. In other processes, the desired product exits the perforation in the drum 100.

In some embodiments, there is a means to remove fluid and gas from the container 200. For example, in FIG. 4-6, lower vessel 210 has an outlet 219 to allow expanding gas from a fluid or solid freezing agent to escape the closed container 200, such as via a hose (not shown) to be discharged safely away from personnel.

While the apparatus is not intended to be limited to any particular size drum 100, it is most advantageous for drums of more than about 5 gallons capacity, which become awkward and difficult to manually manipulate. More preferably, the drums have capacities of 50 or more gallons, and optionally hundreds of gallons. By drum capacity, we mean the volume of fluid that could be contained therein if the lateral surfaces 110 were not perforated. Moreover, the term drum is not intended to be limited to any aspect ratio of range aspect rations of the diameter of the base to the height in the direction of the cylindrical axis.

It should be appreciated that the apparatus 1000 is configured to rapidly process repeated large batches of matter in the drum 100 to provide a high throughput and enhanced economy of scale. It has been appreciated by the inventor that as the drum is enlarged to process larger batches of material, a limit to overall productivity is delays in loading and unloading the drum 100, as well as the end products, which are either retained in the drum 100 or exit the perforation 111 in the drum 100 to be retained in the container 200.

Accordingly, various embodiments provide for the apparatus 1000 to first orient the drum 100 with the opening of side 100e at the rim 118 disposed above the base 100b of the drum 110 to gain the advantage of gravity to feed starting material into the drum 100. The apparatus 1000 is then operative to dispose the drum 100 with the cylindrical axis 100a in a generally horizontal orientation for rotation by the shaft 116 connected to the base 100b to effect separation. Thereafter, when the process of separation is complete the drum 100 can be invented from the loading vertical orientation, so spent material falls out of the drum 100 opening defined by the rim 118 thereof at end 100e.

It should be noted that when the drum 100 is rotated in a generally horizontal orientation product that exits the perforations 111 will fall downward into the lower vessel 220.

Hence, to further improve process efficiency in some embodiment it is also desirable to invert the lower vessel 220 to use gravity to remove the separated product, but in most embodiments after the drum 100 is removed from the lower vessel 220 vessel that forms a part of the container 200.

Further, the apparatus 1000 and methods of use described herein my use several drums 100 in associate with a single container 200, as one drum 100 may be filled or emptied of matter with the alternate identical drum is being rotated with the container 200.

Figure 5:
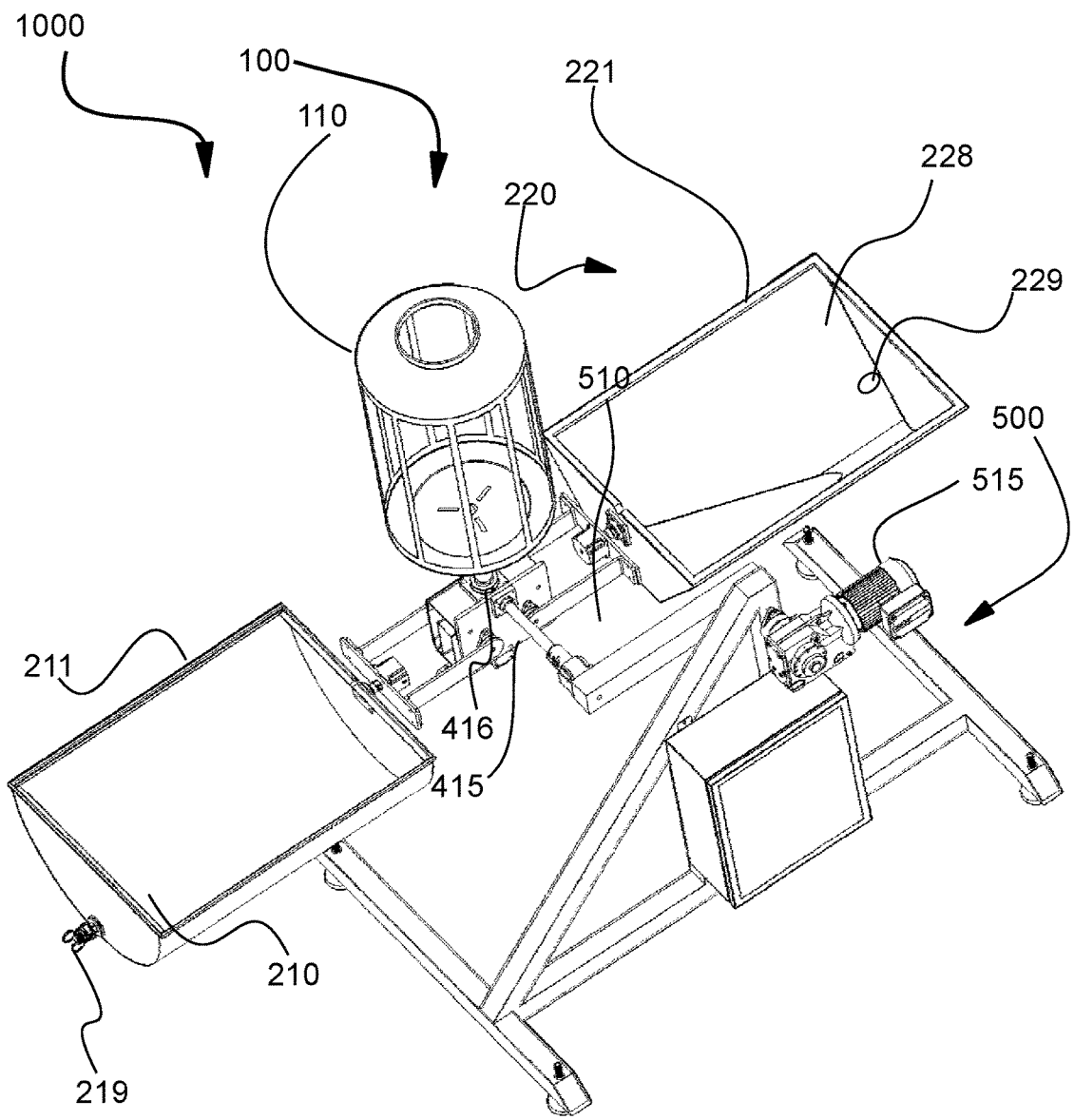
FIG. 5 is a perspective view of the embodiment of FIG. 3 in which the drum is disposed for loading as in FIG. 1D and FIG. 2D.

It is also preferable that at least the lower vessel 220 has an expanse 228 below the rim 221 with a funnel like shape for aid in the flow of solid or fluid material to converge at a sealable drainage portal 229. The drainage portal 229 can thus remove solids, slurries of solid in a fluid, and fluid from the container 200 without inversion. This drainage portal 229 preferably has an external coupling and valve, such as shown at outlet 219. FIG. 5 illustrates a non-limiting embodiment of the expanse 228 of the lower vessel 220 with an irregular polygonal shape below the rim 221. Outlet 219 is at the lowest elevation of the multiple downward sloping polygonal slides that form the expanse 228. The sides that form the expanse 228 may be any combination of linear, curvilinear, and curved shapes to aid in the flow of solids and liquids to the drainage portal 229.

In the embodiments of FIG. 1A-E, FIG. 2A the container 200 is closed and surrounds the drum 100 when the drum is disposed is spun about axis 100a in the separation process. Preferably container 100 has a means to admit a freezing agent before or during this process. The freezing agent is preferably inert and can be admitted as a gas, fluid or solid into the cavity between the closed container 200 and the drum 100, as well as directly into the drum 100. Various means of admitting such freezing agents into a rotary separation apparatus are disclosed in the commonly owned U.S. Pat. No. 10,512,938B2 which issued Dec. 24, 2019, and which is incorporated herein by reference. Further, commonly owned U.S. Pat. No. 10,507,223B2 which issued Dec. 17, 2019, also discloses the process conditions for using a rotary separation apparatus for various application and is also incorporated herein by reference.

Figure 2B:
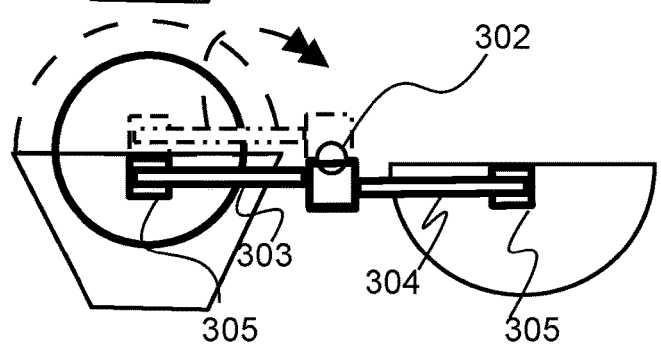
Figure 2C:
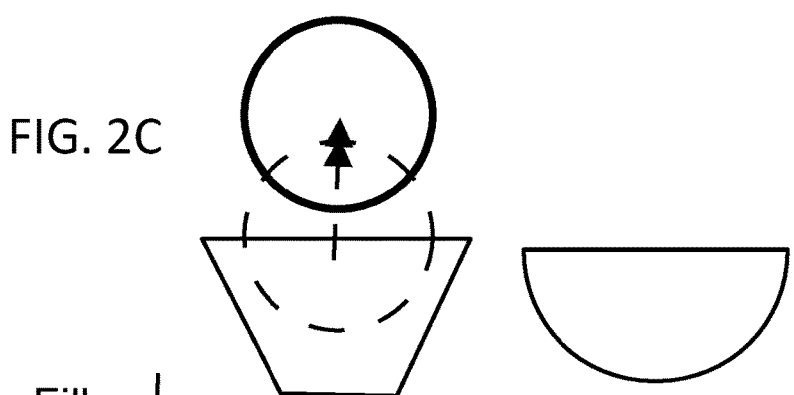
Figure 2D:
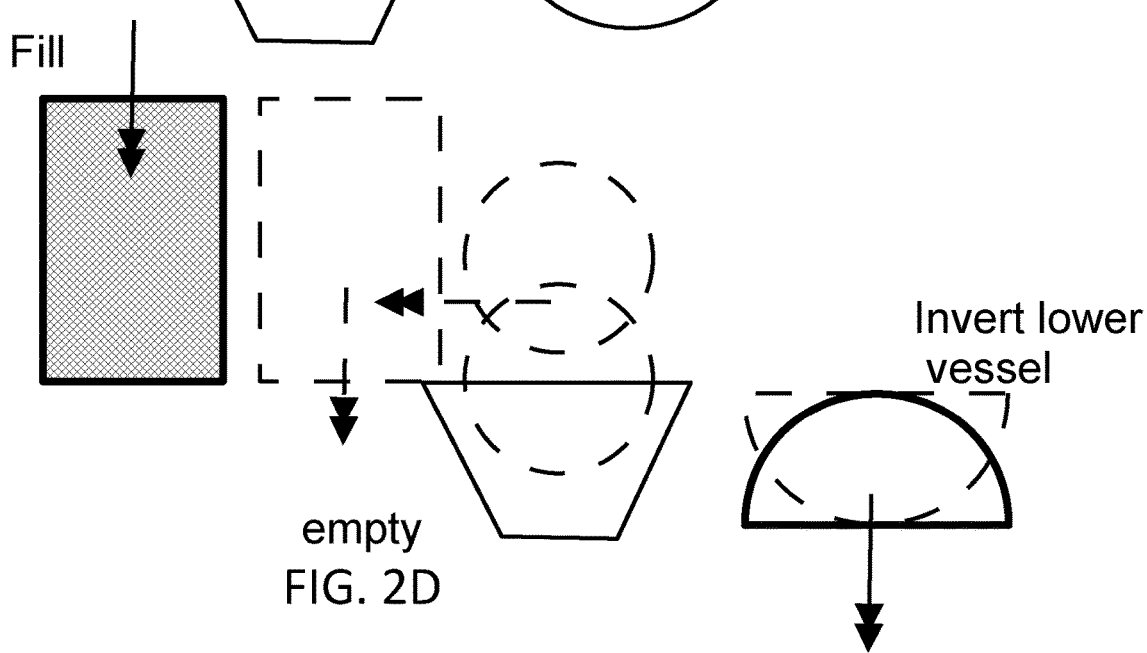

After the separation process is complete, it is necessary to remove product from either or both the drum 100 and container 200, and then recharge the drum 100 with fresh material to be processes, as illustrated in FIGS. 1D and 2D.

FIGS. 1B and 1E illustrate the upper vessel 220 being rotated at a side hinge 301 to invert and be spaced adjacent the lower vessel 201. The hinges 301 and 302 are spaced away from the vessel 210 and 220 by arms 303/304. The ends of the arms 303/304 may have motors or gears 305/306 to rotate and invert either or both vessels 210 and 220.

It should be noted in FIG. 2B that a means to engage and separate the upper and lower vessels may deploy an edge hinge 302 that connects the common rims at a side parallel with the primary axis 100a. Alternatively, as in the embodiments of FIG. 1A-D and FIG. 3-12, the vessels 210 and 220 may separate at a hinge 301 disposed at the common edge of the rim transverse to the primary axis 100a. In any such means, the hinges 301 and 302 comprise a rotary joint that is preferably spaced apart from the rim of both the upper and lower vessel such that the inverted upper vessel is spaced apart from the lower vessel when said means has been deployed.

In step 1C or 2C, the drum 100 can also be lifted, moved, and inverted by well know machines used to handle and manipulate industrial and storage drums that are solid to contain fluid contents, as well as other material. Non limiting examples of such machines are disclosed in the following US Patent documents that are incorporated herein by reference: U.S. Pat. No. 2,645,372 (issued to Broesdma, J. C. on 1953 Jul. 14) U.S. Pat. No. 3,410,431 (issued to Vik, A. M. in 1968 Nov. 12), U.S. Pat. No. 3,448,800 (issued to Howard, W. E. on 1969 Jun. 10), U.S. Pat. No. 6,0245,529 (issued to Kristensen, A. on 2000 Feb. 15) and U.S. Pat. No. 10,450,176 (issued to Beard, T. E. on 2019 Oct. 22). The machines disclosed in these published patents or applications show various ways to provide a capability to lift, move and invert drums or barrels, as well as separating them from the opened container. These machines and the instant invention may use hydraulic actuators or motors, that is electric dynamo machines in places of each other.

It is also preferable to provide a means to invert at least one of the upper 220 and lower 210 vessel after they have been separated. It should be appreciated that the terms upper and lower are relative, as the vessels that form the container 200 can be inverted when the drum 100 is disposed therein.

It is also preferable to provide a means to invert both the upper 220 and lower 210 vessel, as shown in FIGS. 1D and 2D. This may be desirable to clean the vessels 210 and 220 from any interior residue, as well as for to clean with fluids and drain the fluid used in cleaning. The upper vessel 220 may also have a port 2291 that can be used for drainage or to locate a thermal sensor for monitoring the temperature of the contents as cooling by the freezing agent used in the process.

It is also preferable to provide a means to invert the drum 100 to discharge material from one end 100e that configured to be opened at rim 118. The end 100e is disposed transverse to the principle axis 110a, opposite base 100b.

The drum 100 can then be reloaded with fresh matter for separation in this upright orientation. In the next step in the process, when the drum 100 has been reloaded with fresh plant or botanical matter and the opening closed, it is also preferable to provide a means to dispose the drum 100 in the lower vessel 220 and dispose the upper vessel 210 to engage the lower vessel 220 at the common rims drum 100 with a rotary drive means. Such rotary drive mean may include a shaft that passes through container 200 and engages a base of the drum.

In the embodiment of FIG. 3-12 various actuators provides the means to rotate the drum 100, invert the drum 100 and dispose the drum 100 in the container 200.

Figure 9:
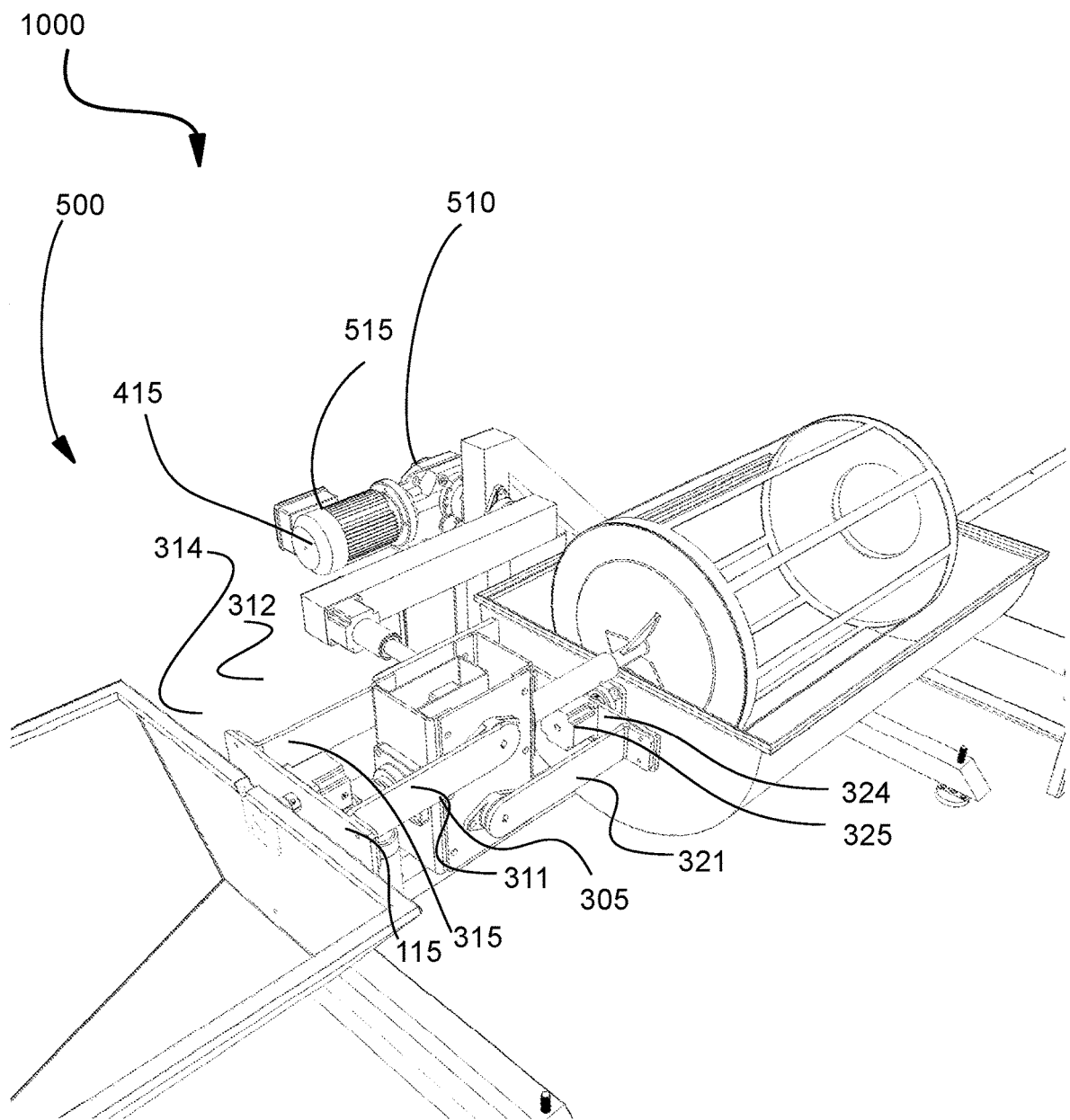
FIG. 9 is an expanded perspective view of an embodiment of an actuator.
Figure 10:
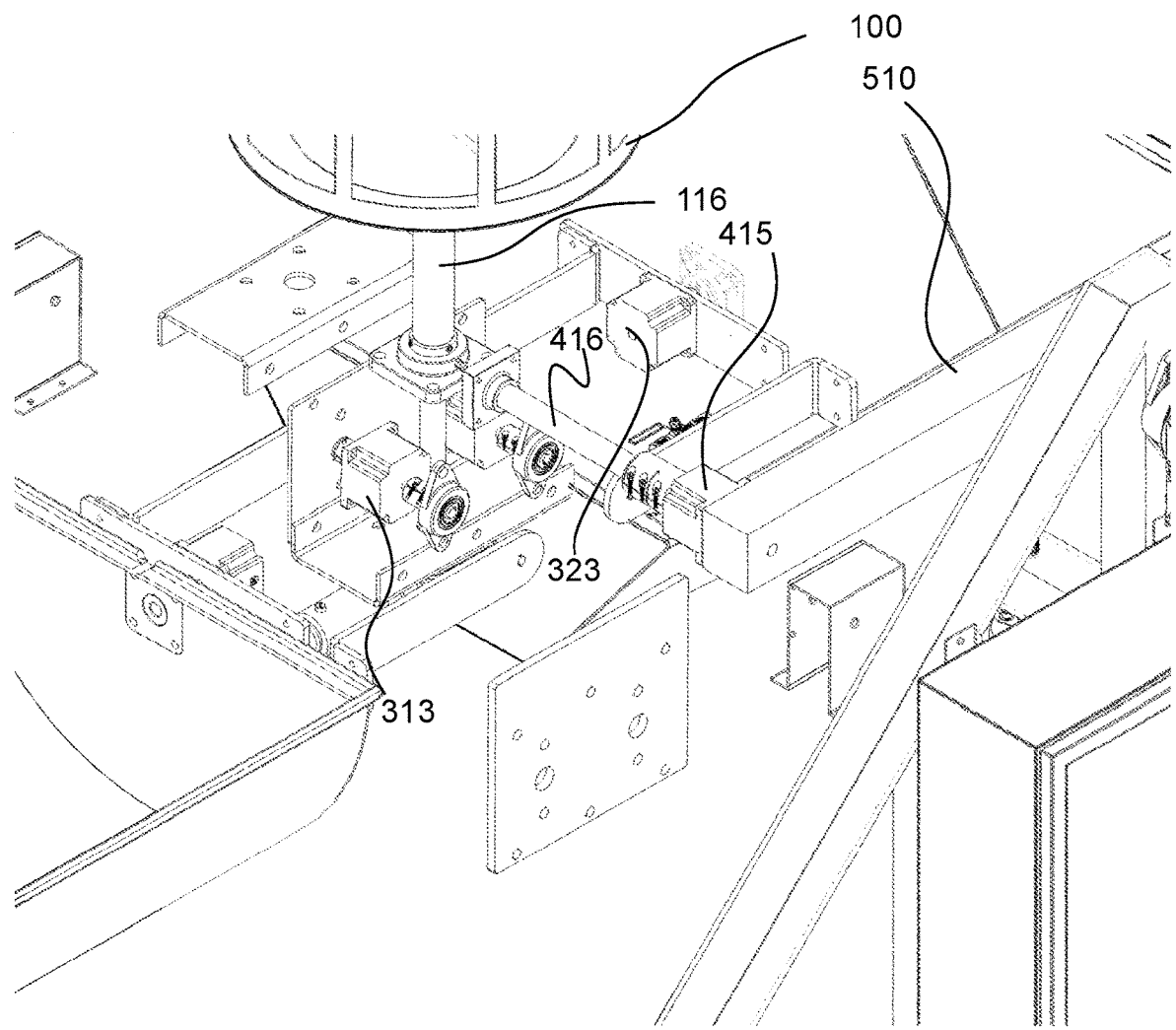
FIG. 10 is a partially exploded perspective view of the actuator of FIG. 9.
Figure 11:
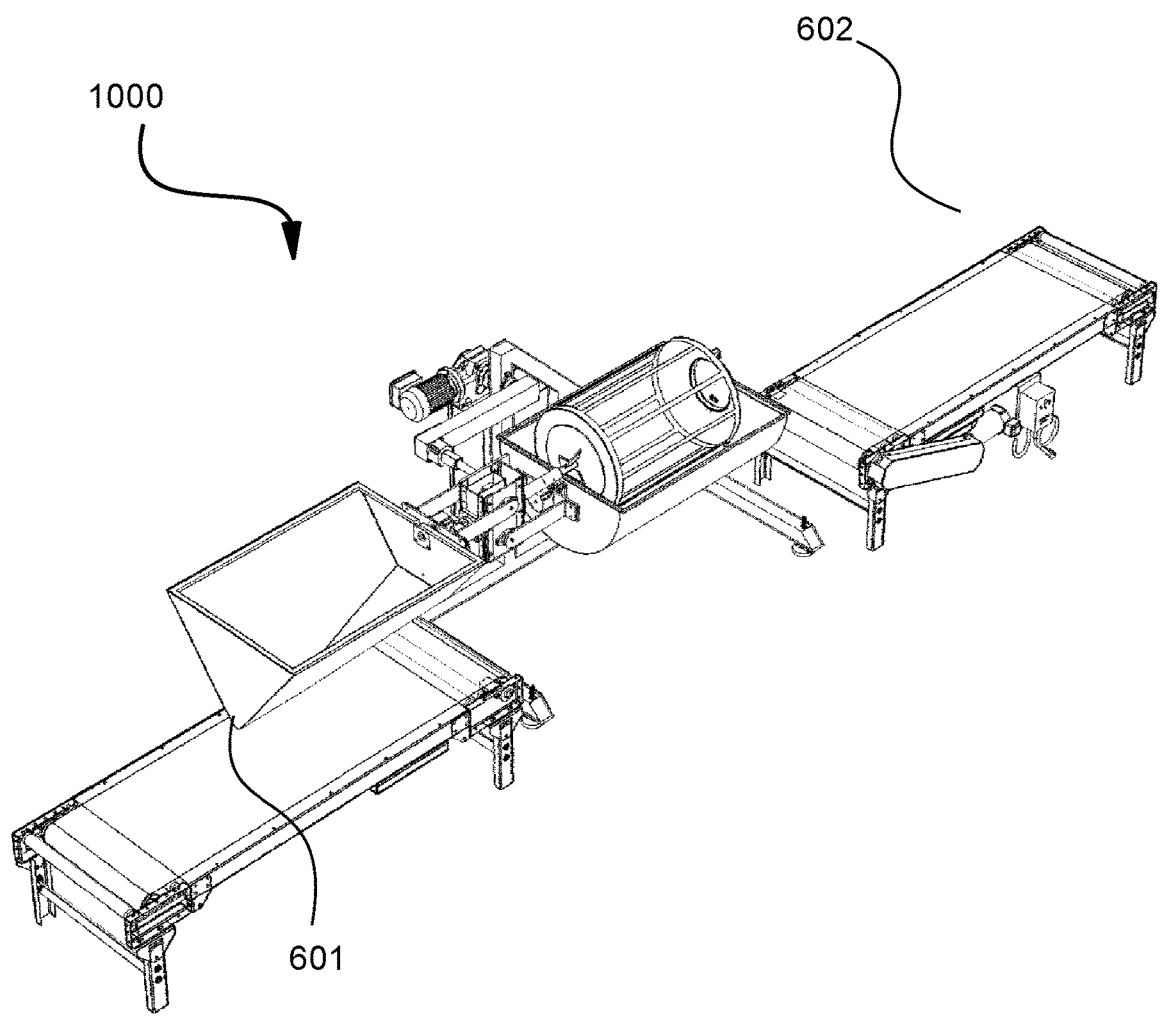
FIG. 11 is a front perspective view of another embodiment of the invention that includes a pair of conveyor belts disposed to receive product from each of the vessels that form the container.

It should also be appreciated that in the embodiment of FIG. 3-12, a series of actuators have the means to rotate and invert the upper and lower vessel as well as the drum. In some embodiments these means include a common actuator 300, which is illustrated in more detail in FIGS. 9 and 10, showing a common housing 305 that supports a cluster of motor that are configured for independent opening of the container 200, removal of the drum 100, and rotation of the vessel(s) 210/220 that form the container 220 to remove the contents, such as onto the conveyor 601 and 602 of FIG. 11-12. The drum 100 may be filled by another conveyer 603 by lifting material in hopper 604 to drop into the opening at the rim 118 when the cap or cover 117 is removed or raised.

The common actuator 300, which acts as hinge 301, provides cantilevered support for each vessel 210 and 220 via pair of arms 310 and 320 that are each in hinged connection on opposing sides of the housing 305. The arms 311 and 312 of pair 310 respectively connect opposing sides of the housing 305 to dual shafts of motor 313 fixed within the housing 305. The housing 305 also support bearings for the motor shafts. The pairs of arms 310 and 320 are also in hinged connection to the housing 305 of the common actuator 300 and spaced apart from a central region thereof, being generally paced apart from the other arms 311 and 312 by the same distance from the central region. Either set of arms 311 and 312, and or 321 and 322, can rotated the connected vessel upward and away from the other vessel and/or the drum 100, so the drum 100 can be accessed.

The opposing side of the arms 311 and 312 connect to a common plate 314 that supports another motor 315 that has a shaft coupled to the side of the lower vessel 210. The motor 315 may be energized by a controller 530 to invert the lower vessel 210. The controller 530 may energize all or some of the motors of the various actuator means in the various embodiment in the sequences illustrated in FIGS. 1A-E and 2A-D, among others.

The arms 321 and 322 respectively connect opposing sides of the housing 305 to dual shafts of motor 323. The opposing side of the arms 321 and 322 from the housing 305 are connected to a common plate 324 that support another motor 325. Motor 325 has a shaft coupled to the side of the upper container 220. The motor 325 may be energized by the controller 530 to invert the upper container 220.

A motor 115 at the bottom of the housing 305 has a shaft 116 that is coupled to the base of the drum 100. The shaft 116 passes through the housing 305 between motor 313 and motor 323. The motor 115 may be energized by the controller 530 to spin the drum 100 when it is enclosed in the container 200, in which the upper 220 and lower 210 vessel engage at the gasket 215.

Figure 6:
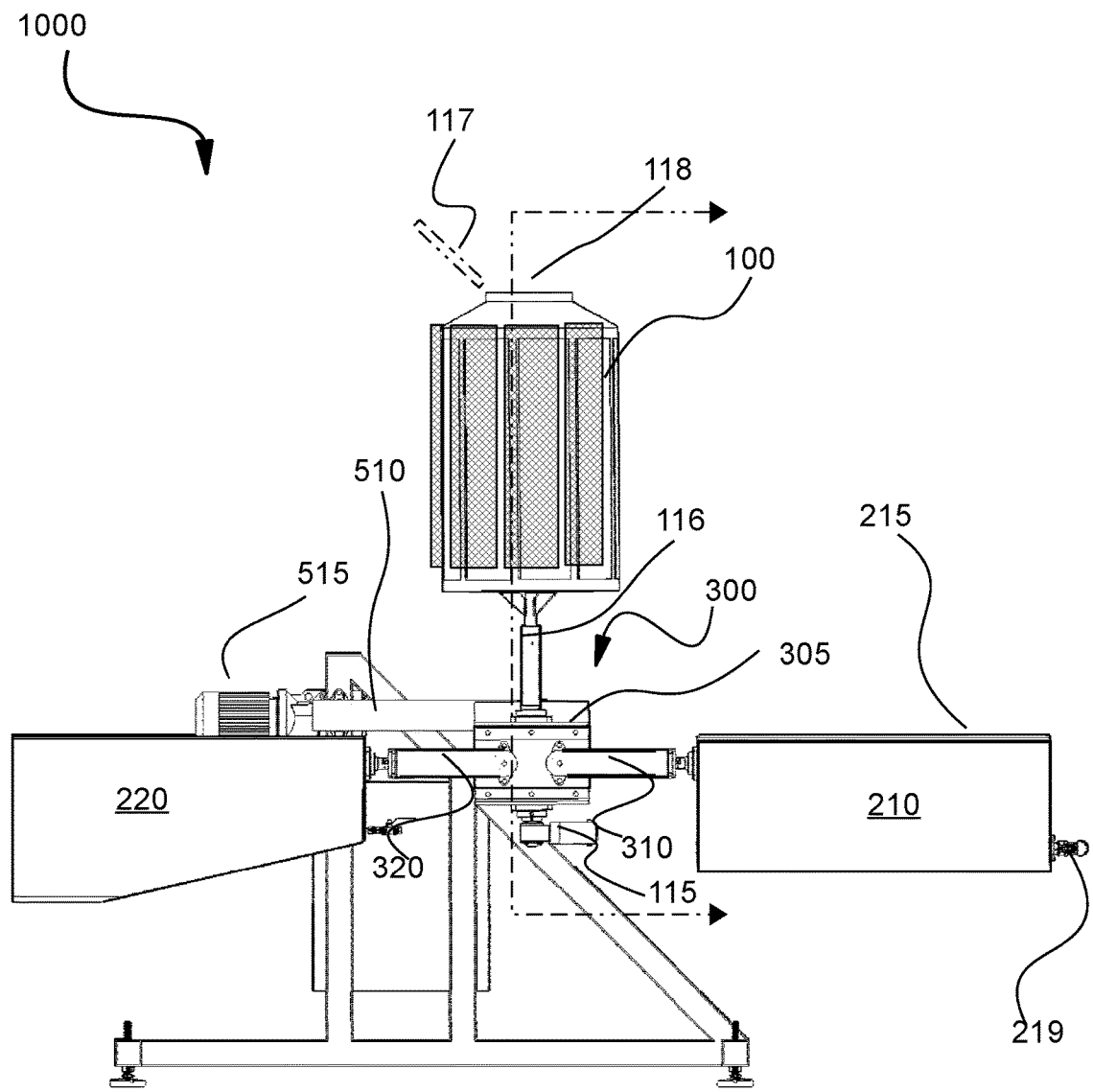
FIG. 6 is a front elevation view of the apparatus in the configuration in FIG. 5.
Figure 7:
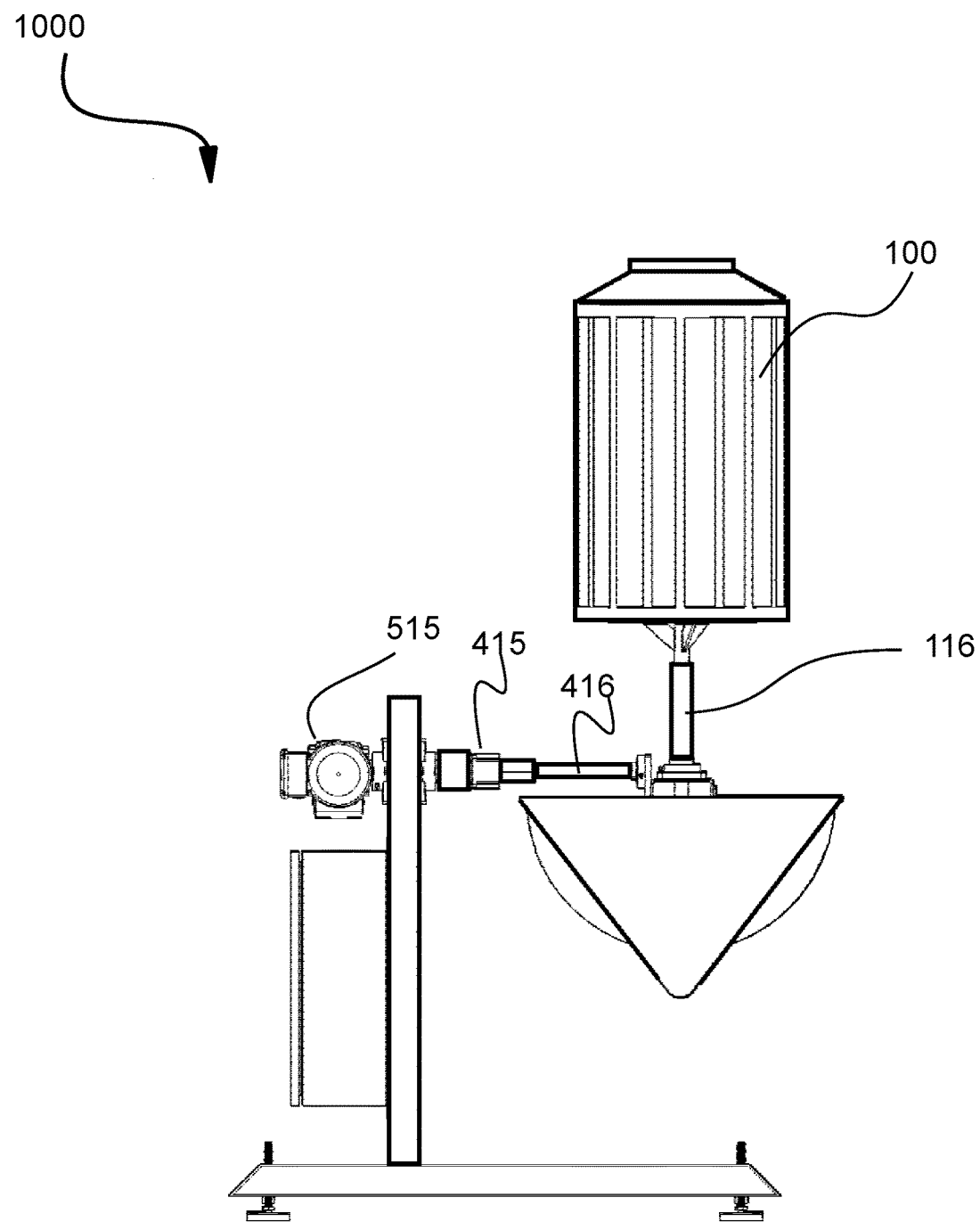
FIG. 7 is a side elevation view of the apparatus in the configuration in FIG. 5.
Figure 8:
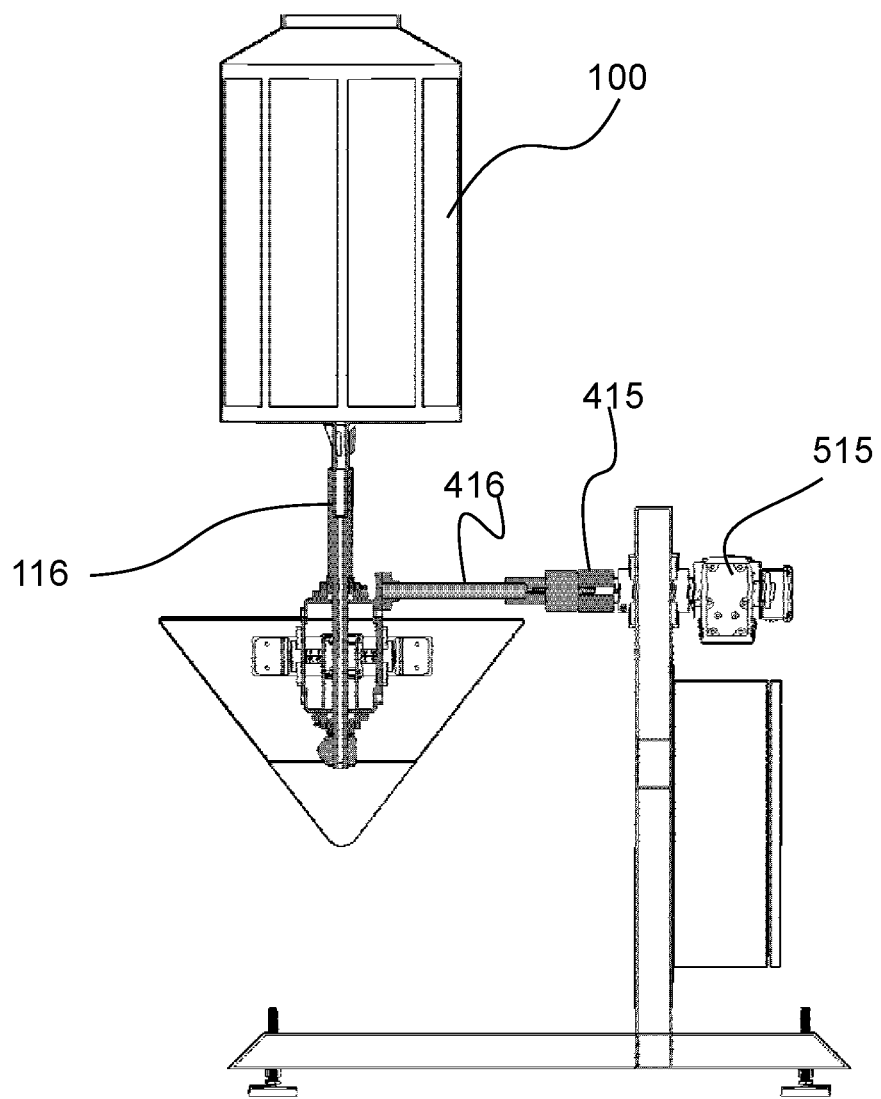
FIG. 8 is a rear cross-sectional elevation view of view of the apparatus in the configuration in FIG. 5 taken at the broken section line in FIG. 6.

An external motor 415 is provided to turn a shaft 416 that is coupled to the exterior of the housing 305 and is thus capable of rotating the drum 100 by 90 degrees from a vertical orientation of the axis 110a in FIG. 6 to the horizontal orientation in other Figures. The external motor 415 is mounted at an end of a primary arm 510

A motor 515 is disposed opposite end of a primary arm 510 than motor 415. The axis of rotation of motors 415 and 515 are parallel. A hinge couple or bearing structure, which is optionally part of the motor 514 that is coupled to a support structure 500 such that the load of drum 100 and container 200, along with actuator 300 are transferred to the ground. The primary arm 510 is configured to rotate raise or lower the drum 100 and container 200 when the motor 515 is energized by the controller 530. The controller 530 may be mounted in the support structure or frame 500.

Figure 3:
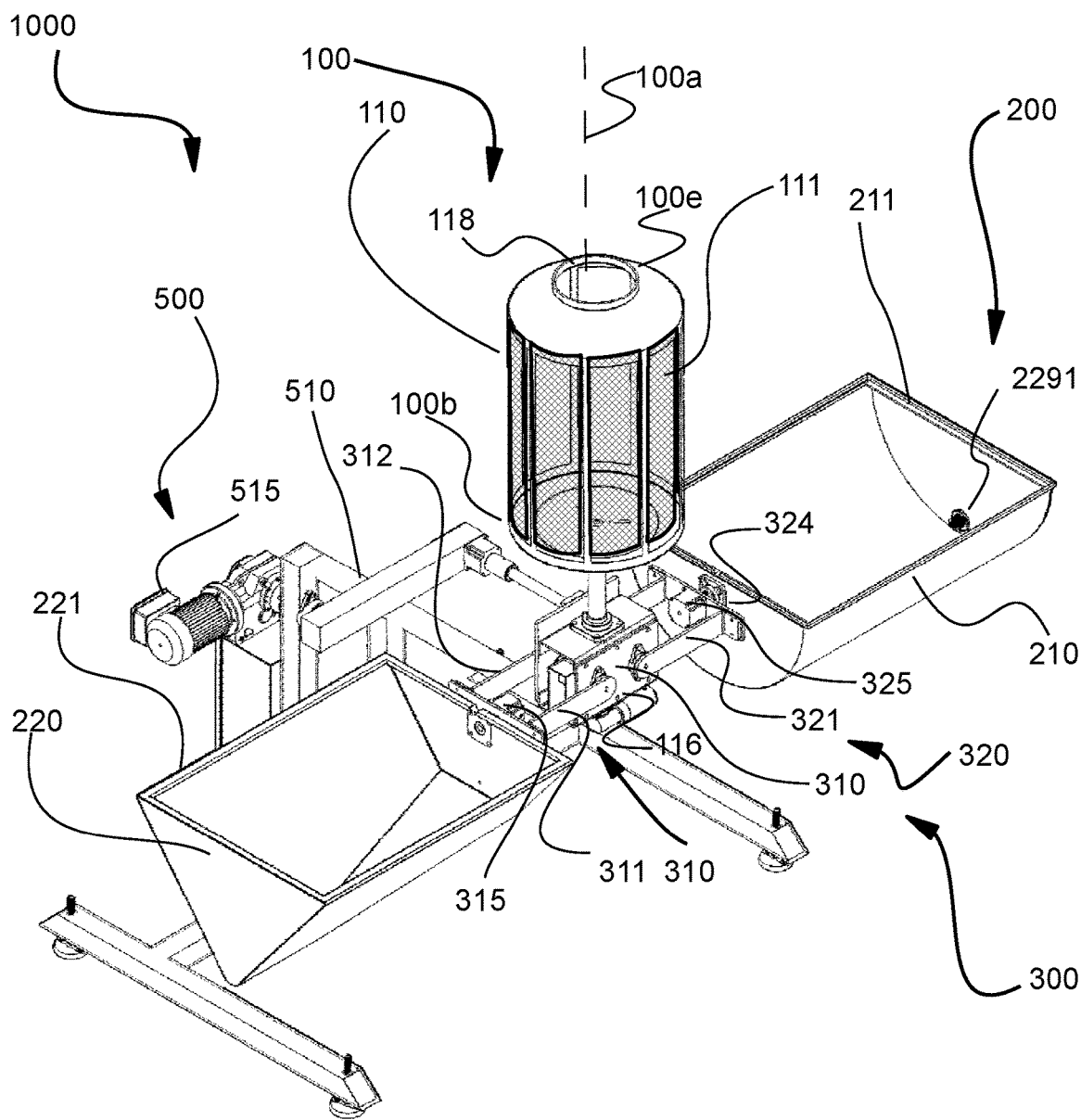
FIG. 3 is a front perspective view of another embodiment of the invention.
Figure 4:
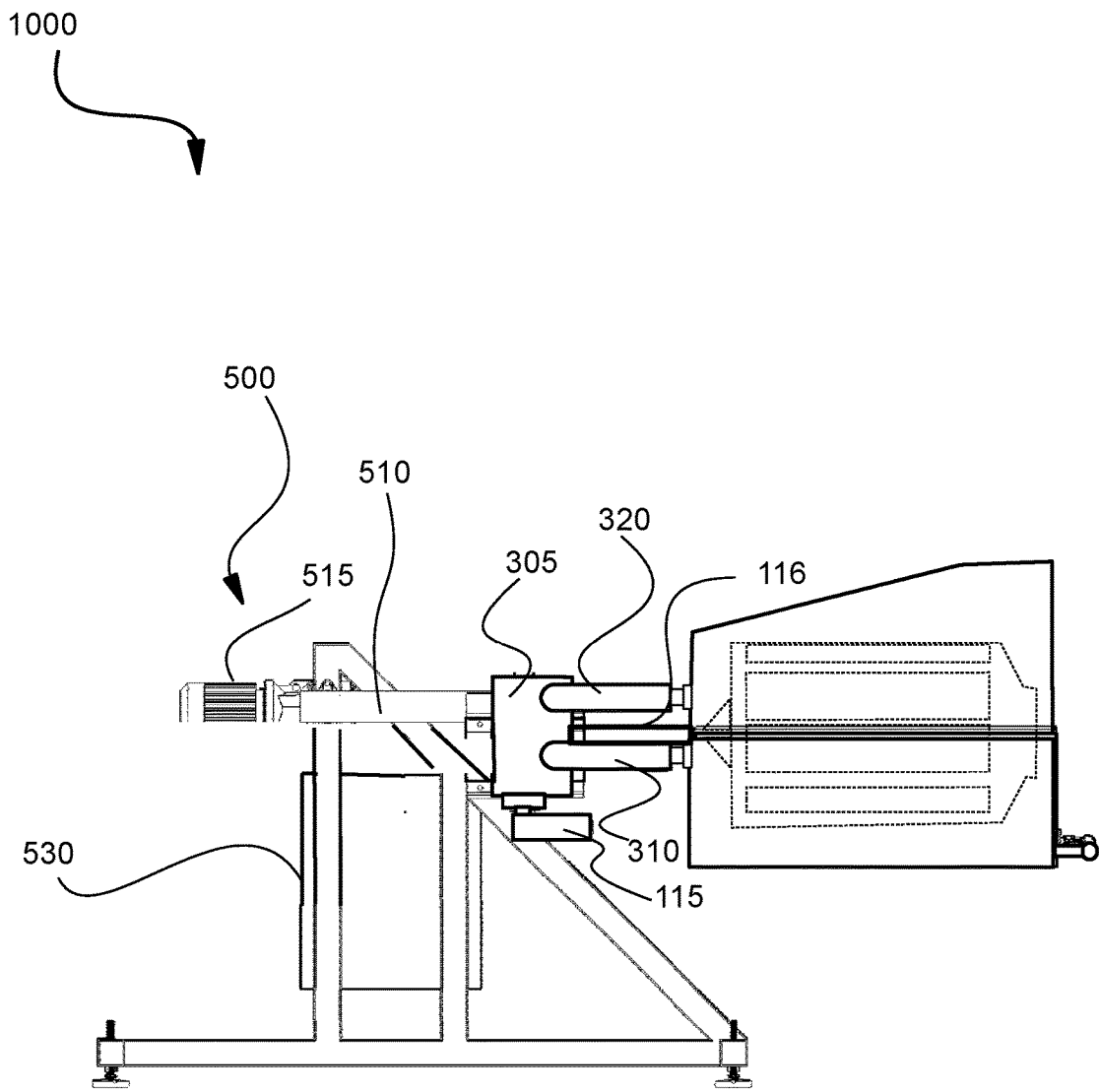
FIG. 4 is front elevation view of the embodiment of FIG. 3 in which the container is closed around the drum.

The opposing end of arm 510 supports the external motor 415 that rotates the shaft 416 and can also rotate the common actuator 300 by 180 degrees relative to the position in which it is disposed the filling orientation with the rim 118 above the opposing side as in FIG. 3 among other. The primary arm 510 can rotate 90 degrees to raise the common actuator 300 and the attached drum 100 and container vessels 210 and 220. Then the attached drum 100 can be inverted.

Hence, motor 515 together with motor 415 provide a means to invert the drum 100 after it is removed from the lower vessel 220 by raising the common actuator via arm 510, being rotated to the vertical orientation by motor 515. Then motor 415 can then rotate the shaft 416 by 180 degrees, thus inverting the housing 305. The common actuator 300 may separate the upper 220 and lower 210 vessels by rotating one by at least about 120 to about 160 degrees with respect to the other.

In general, wherein the one of more actuators includes a first motor and second motor in which the first motor is operative to rotate the upper vessel away from the lower vessel and the drum is rotated between the vertical and horizontal orientation of the principal axis of the cylinder by the second motor the coupled to a support frame that is external to common housing that contains the first motor to rotate the common housing at least 60 degrees.

The drum 100 has a cap or cover 117 over a portion of one end of what may be considered an upper base. The cap or cover 117 may be removed manually or by the controller 530 via energizing or de-energizing a latch hinge to open the drum 100 at rim 118. The lower base of the drum 100 is couple to a rotary shaft 116 of the actuator 300 that is used to spin or rotate the drum at the desired speed within the container 100.

Figure 12:
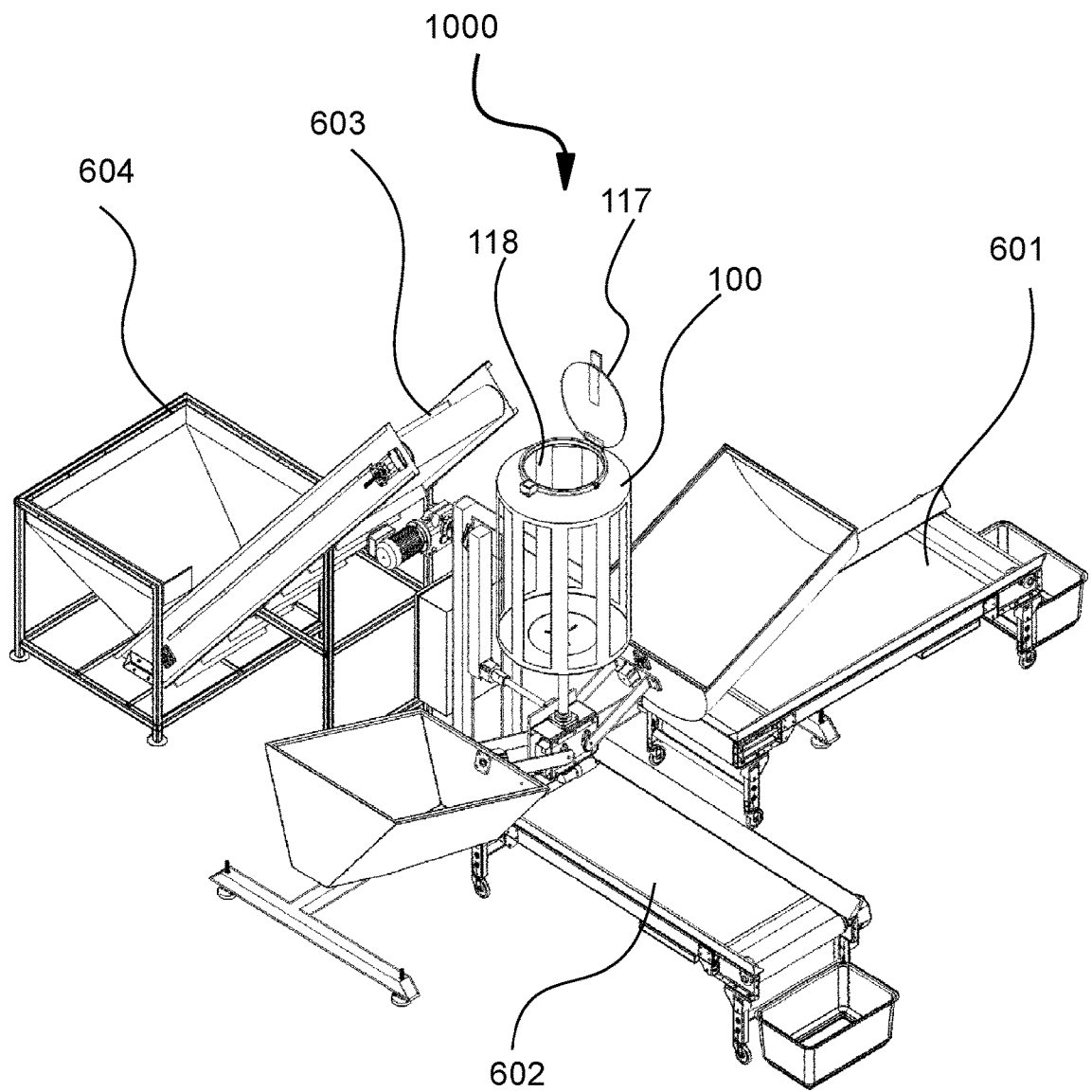
FIG. 12 is a front perspective view of another embodiment of the invention that includes a different pair of conveyor belts disposed to receive product from each of the vessels that form the container and a conveyor to fill the drum.
Figure 13:
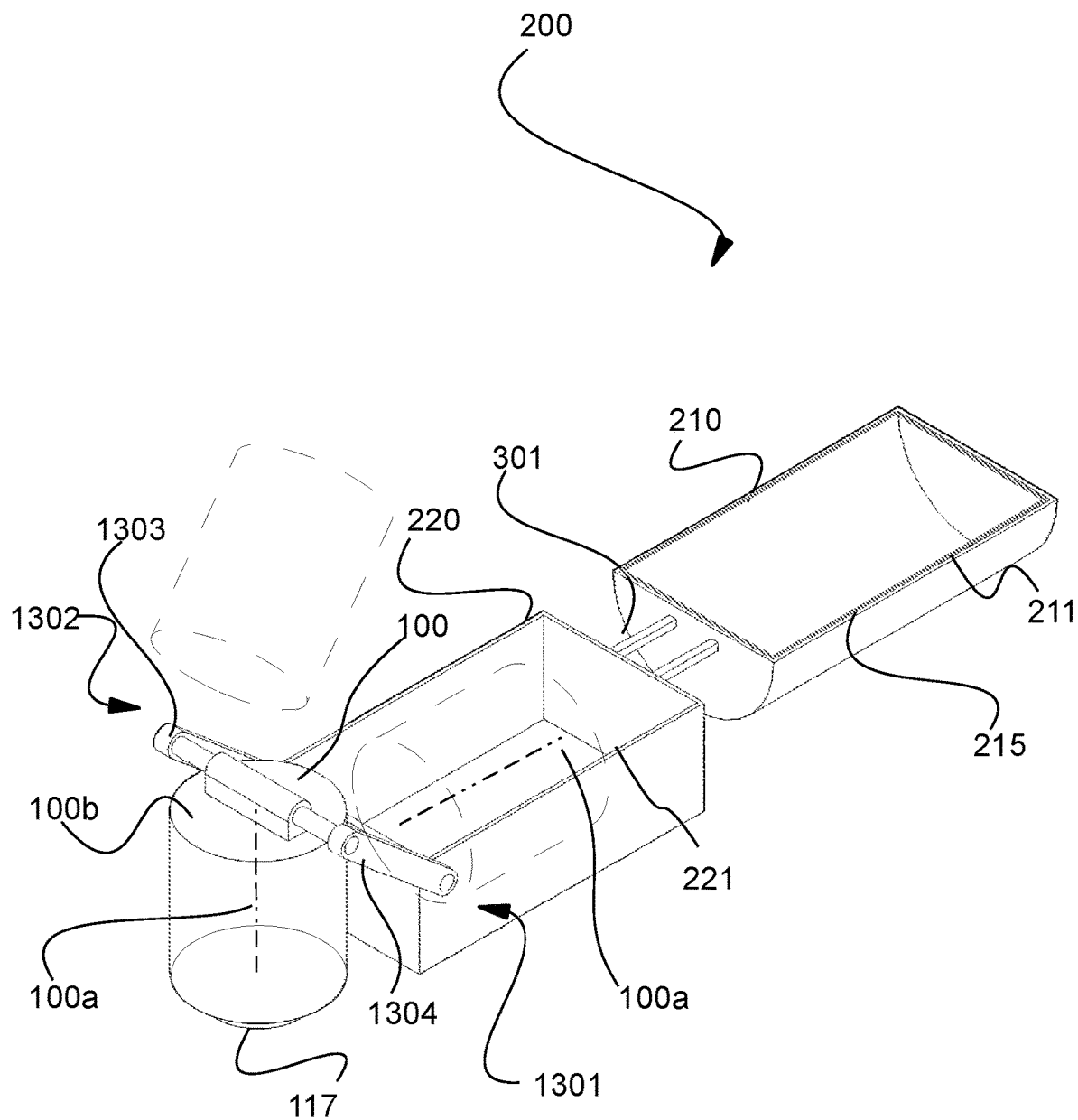
FIG. 13 is a schematic perspective view of another embodiment of the apparatus.

FIG. 12 illustrated how the drum 100 may be supported upright with the cap or cover 117 released to provide the opening for filling via the conveyor 603. While axis 100a is vertical in this figure, the drum may also be filled when the axis 110a is tilted upright 45 degrees from the horizontal positions, as well as intermediate positions. All of the collection baskets and source feeds, such as conveyors, may be supported on digital scale to provide for repeated filing of the drum 100 in each batch, as well as weighting the product of each production cycle to log the yield and other process variables.

The drum 100 is preferably instrumented with one or more thermal sensors to provide a consistent degree of cooling before the separation process starts.

FIG. 13 to 15B schematically illustrate variants of the apparatus 100 with alternative means to lift, move and turn/invert the drum 100. In these embodiments the container 200 forms an enclosed space around the drum 100 when the drum 100 is disposed with the principal axis 100a in a horizontal orientation In FIG. 13-14, the container 200 is formed of an upper 210 and a lower 220 vessel that mate via a hinge 301 at common junction of their respective rims 211 and 221. A gasket 215 is disposed on one of the rims 211 or 221 such that a fluid tight seal is formed when the common actuator 300 is deployed to urge the rims 221 and 211 into contact.

The container 200 opens as in the embodiments of FIG. 1A-D and FIG. 3-12, such that the vessels 210 and 220 may separate at a hinge 301 disposed at the common edge of the rim transverse to the primary axis 100a. The hinges 301 and 302 comprise a rotary joint that is preferably spaced apart from the rim of both the upper 210 and lower vessel 220 such that the inverted upper vessel 210 is spaced apart from the lower vessel 220 when said means has been deployed.

When the upper vessel 210 is inverted and removed from the lower vessel 220, an actuator 1301 is configured to remove the drum from the container in the opposite direction, deploying a hinge mechanism 1302 to flip the drum 100 orientation 180 degrees, first to a vertical orientation and then horizontally, and optional to flip the drum 100 another 90 degrees to invert it.

After the drum 100 is filled via the opening formed when the cap 117 is removed from rim 118, the actuator 1301 is operative to reverse the movement and return the drum 100 to the container 200. The hinge mechanism 1302 coupled the drum base 110*b* to the sides 210*s* of the upper vessel 210 via a pair of rotating arms 1303 and 1304. Each end of the arms 1303 and 1304 are configured for independent rotation from the other end to first lift the drum 100 from the lower vessel 220 by rotation of the arms 1303 and 1304 at the coupling to lower vessel 220. Then, the arms 1303 and 1304 are rotated at the coupling to the base 100*b* to invert the drum 100.

Figure 15A:
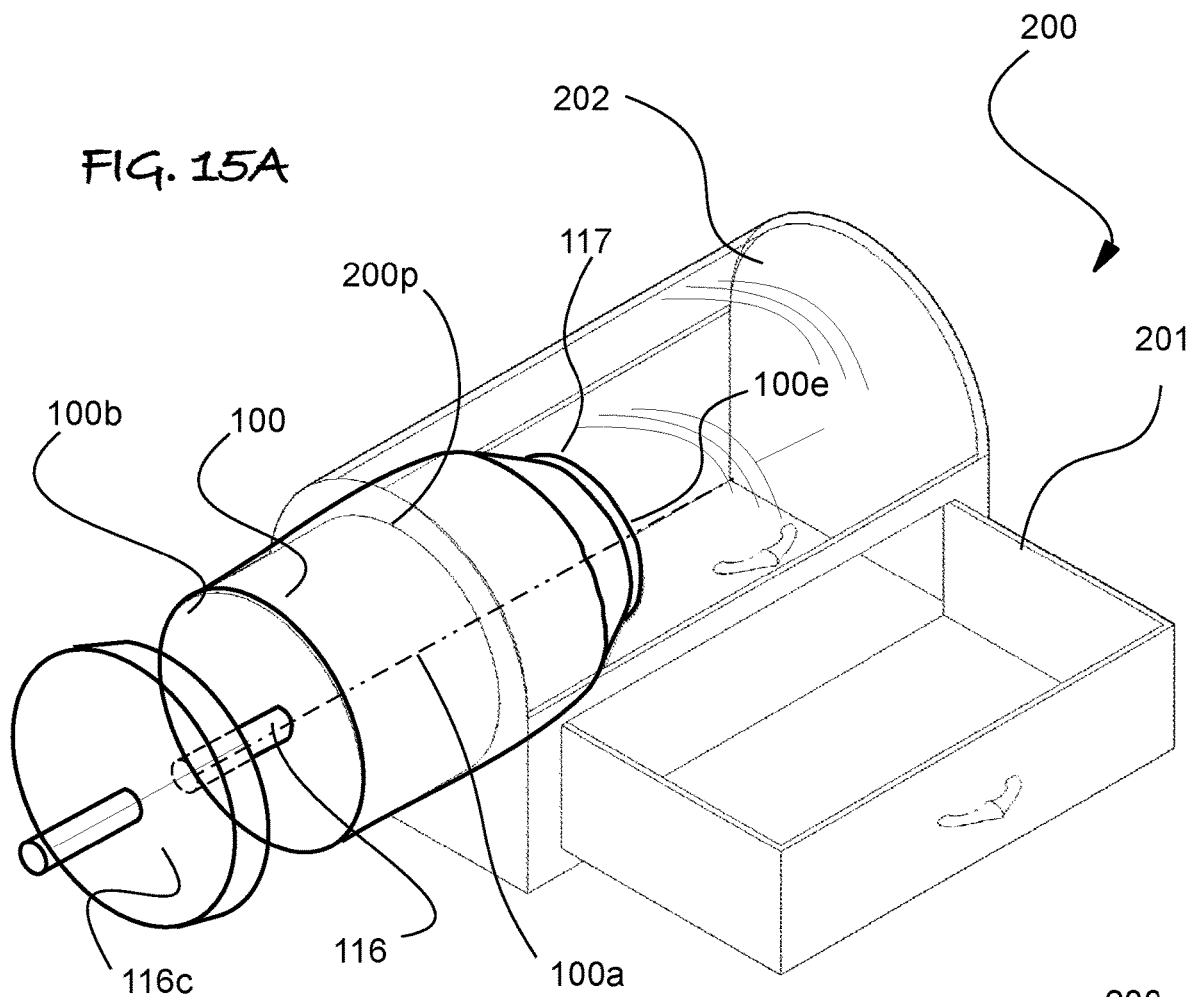
FIG. 15A is schematic perspective view of another embodiment of the apparatus illustrating moving between alternative positions inside and outside.
Figure 15C:
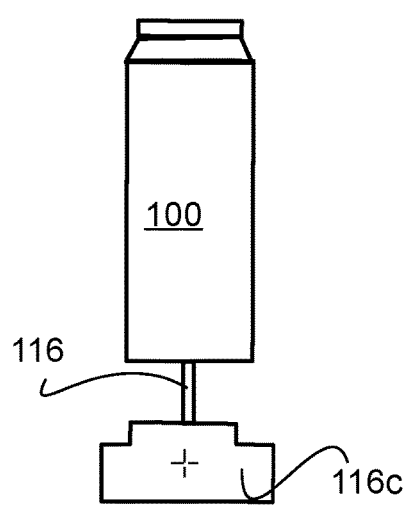
FIG. 15B is a schematic sectional view of the drum in the container whereas in FIG. 15C the drum is schematically illustrated in a section view outside the container and rotated to the vertical orientation.
Figure 15B:
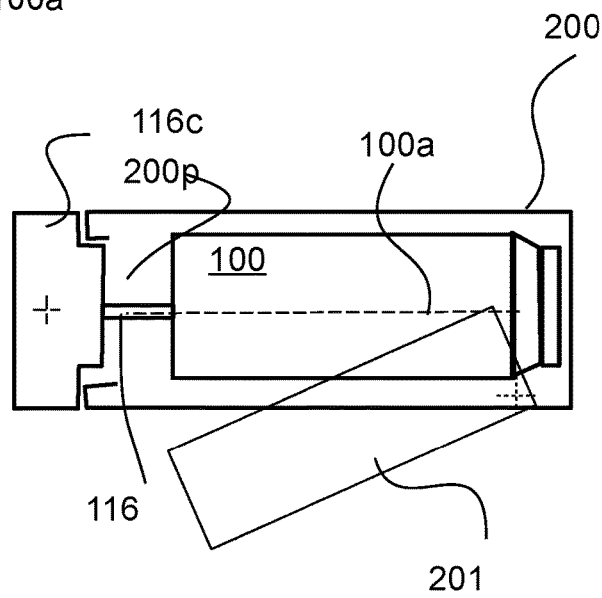
Figure 16:
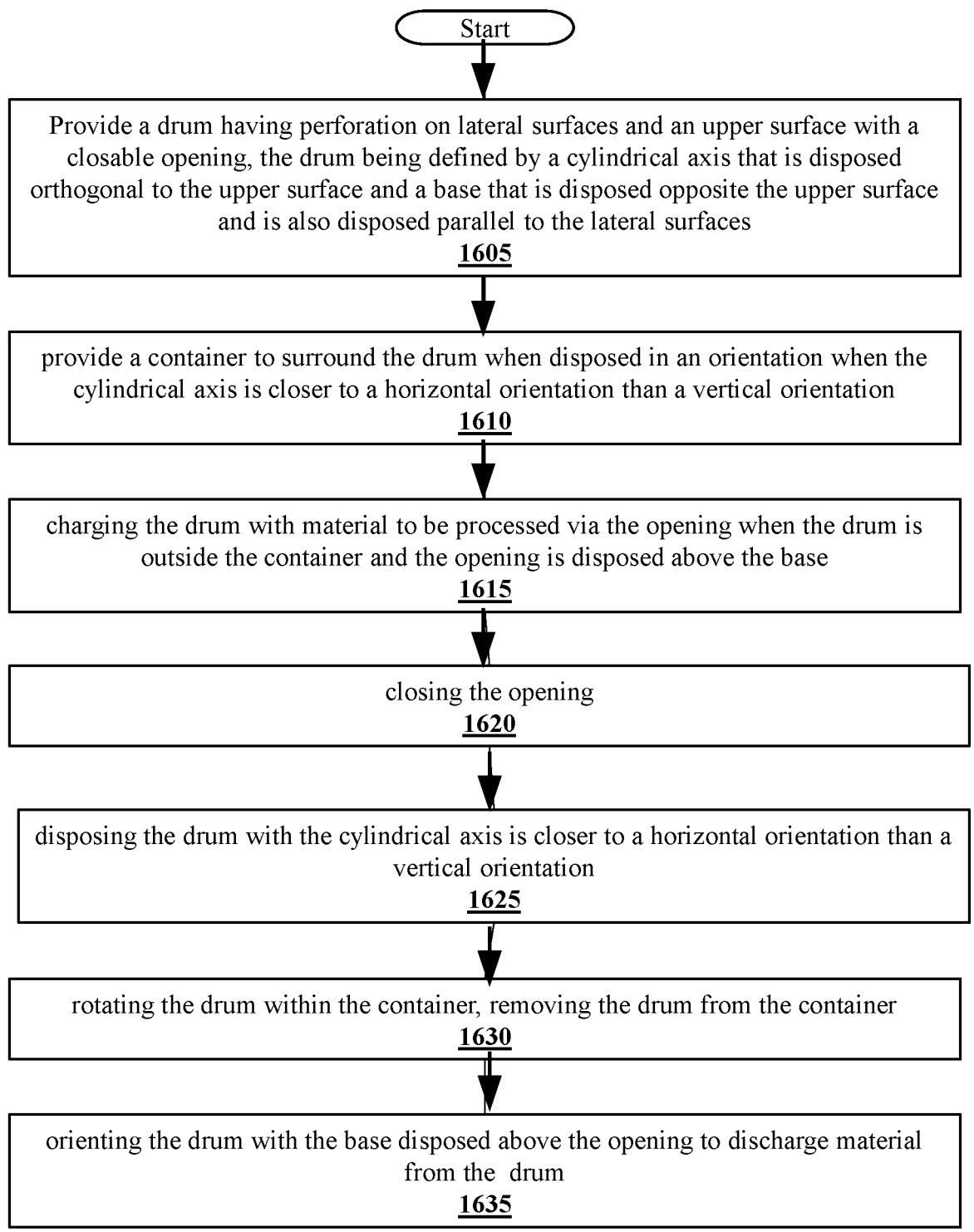
FIG. 16 is a flow chart of an embodiment of the method illustrated in FIGS. 1A-E and 2A-D.

In FIG. 15A-15C, the container 200 comprises in a lower portion a drawer 201 that translate away from the lower portion of the container 200 to provide access to material collected therein. In FIG. 15A, the drawer optionally slides laterally away from the side of the lower portion to provide access for removing material that collected in the drawer after exiting the drum 100 via the perforations 100. Alternatively, as shown in FIG. 15B, the drawer 201 may also be a portion of the lower container or an insert therein that is in hinged engagement to swing away from the lower contains and thus act as a shoot to pour the collected material downward toward a conveyor or vessel. A hinged cover 202 may be arranged on an upper portion of the container 200 above the drawer 201 to clean the container 200. The container 200 may also be configured to be separated for cleaning by a lateral seam that defines an upper and lower vessel, or a vertical seam.

The drum 100 is removed or inserted in the container 200 laterally via a side portal 200*p* such that it translates in the direction of the principal axis 100*a*. Alternatively, the drum 100 can be fixed, and the container 200 can translate laterally. The portal 200*p* may be sealed by a cover 116*c* that support the shaft 116 coupled to the drum base 100*b* for rotating the drum 100, which then is optionally coupled in rotatory engagement to a motor (not shown) on the opposite side of the cover 116*c* from the drum 100. The opposing side 100*e* of the drum 100 may have the cap 117 that is removed to load or unload material. FIG. 15C illustrates the cover 116*c* and drum 100 connected via the shaft 116 with the axis 100*a* vertical to fill the drum via end 100*e* when the cap 117 is removed. The drum 100 can inverted to be emptied by the same actuator that rotates the cover 116*c* after the drum 100 is removed from the container.

While the invention has been described in connection with several embodiments, it is not intended to limit the scope of the invention to the particular form set forth, but on the contrary, it is intended to cover such alternatives, modifications, and equivalents as may be within the spirit and scope of the invention as defined by the appended claims.

I claim:

1. A rotary separation apparatus comprising:
   a drum having a generally cylindrical shape with a principal axis coincident with the principal axis of a cylinder defined by the generally cylindrical shape, in which the drum has lateral surfaces with a plurality of perforations and a base of the cylinder that is opposed to an upper end of the cylinder;
   a container that forms an enclosed space around the drum when:
      the drum is disposed with the principal axis in a horizontal orientation, and
      an upper and lower vessel are brought into mutual engagement at a rim of the upper vessel to a rim of the lower vessel;
   one or more actuators that are operative to modulate the orientation of the principal axis of the cylinder from between an upright and inverted vertical orientation and dispose the drum horizontally in the container; and
   a means to rotate the drum about the principal axis when the drum is disposed horizontally within the container,
   wherein the lower vessel is capable of being inverted from an upright horizontal orientation to a downward facing horizontal orientation by the one or more actuators to empty the lower vessel.

2. A rotary separation apparatus comprising:
   a drum having a generally cylindrical shape with a principal axis coincident with the principal axis of a cylinder defined by the generally cylindrical shape, in which the drum has lateral surfaces with a plurality of perforations and a base of the cylinder that is opposed to an upper end of the cylinder;
   a container that forms an enclosed space around the drum when:
      the drum is disposed with the principal axis in a horizontal orientation, and
      an upper and lower vessel are brought into mutual engagement at a rim of the upper vessel to a rim of the lower vessel;
   one or more actuators that are operative to modulate the orientation of the principal axis of the cylinder from between an upright and inverted vertical orientation and dispose the drum horizontally in the container; and
   a means to rotate the drum about the principal axis when the drum is disposed horizontally within the container,
   wherein the one of more actuators includes a first motor and second motor in which the first motor is operative to rotate the upper vessel away from the lower vessel and the drum is rotated between the vertical and horizontal orientation of the principal axis of the cylinder by the second motor that is coupled to a support frame that is external to a common housing that contains the first motor to rotate the common housing at least 60 degrees.

3. The rotary separation apparatus according to claim 2 wherein the means to rotate the drum about the principal axis when the drum is disposed horizontally within the container is a primary motor coupled to the common housing to rotate a shaft that extends through the common housing to connect to the base of the cylinder in which the shaft extends in the direction of the principal axis of the cylinder.

4. The rotary separation apparatus according to claim 2 wherein the one of more actuators includes a third motor that is connected to the support frame and the second motor is mounted at a distal end of a primary arm and the proximal end of the primary arm is connected to the third motor in which the third motor is operative to rotate the primary arm from a horizontal to a vertical orientation before the one of more actuators are operative modulate the orientation of the principal axis of the cylinder from an upright to an inverted vertical orientation.

5. A rotary separation apparatus comprising:
   a drum having a generally cylindrical shape with a principal axis coincident with the principal axis of a cylinder defined by the generally cylindrical shape, in which the drum has lateral surfaces with a plurality of perforations and a base of the cylinder that is opposed to an upper end of the cylinder;

a container that forms an enclosed space around the drum when the drum is disposed with the principal axis in a horizontal orientation;

one or more actuators that are operative to modulate the orientation of the principal axis of the cylinder from between an upright and inverted vertical orientation and dispose the drum horizontally in the container; and a means to rotate the drum about the principal axis when the drum is disposed horizontally within the container, wherein the container is sealed by a portal with a cover that supports an axle that is coupled to rotate the drum about the principle axis and the apparatus is configured to remove the drum via the portal and disposes a motor on the opposite side of the cover.

6. A system for processing materials in a rotary separation apparatus, the system comprising:

rotary separation apparatus that comprises:
- a drum having a generally cylindrical shape with a principal axis coincident with the principal axis of the cylinder defined by the cylindrical shape, in which the drum has lateral surfaces with a plurality of perforations,
- a container that forms an enclosed space around the drum when the drum is disposed with the principal axis in a horizontal orientation,
- one of more actuators to invert the drum when out of the container and dispose the drum horizontally in the container, and
- a means to rotate the drum about the principal axis when the drum is disposed horizontally within the container; and at least a first conveyor belt configured to transport material to an opening in an upper end of the cylinder when the drum is oriented with the principal axis in the vertical orientation.

7. A process for treating materials, the process comprising:

providing a drum having perforation on lateral surfaces and an upper surface with a closable opening, the drum being defined by a cylindrical axis that is disposed orthogonal to the upper surface and a base that is disposed opposite the upper surface and is also disposed parallel to the lateral surfaces, providing a container to surround the drum when disposed in an orientation when the cylindrical axis is closer to a horizontal orientation than a vertical orientation, charging the drum with material to be processed via the opening when the drum is outside the container and the opening is disposed above the base, closing the opening, disposing the drum with the cylindrical axis closer to a horizontal orientation than to a vertical orientation, rotating the drum within the container, removing the drum from the container, and orienting the drum with the base disposed above the opening to discharge material from the container.

8. The process for treating materials according to claim 7 further comprising a step of removing material that traversed the drum lateral surfaces via the perforations from the container.

9. The process for treating materials according to claim 7 where the material that traversed the drum lateral surfaces via the perforations is removed from the container by one of a drawer and shoot that moves away from a lower portion of the container.

10. The process for treating materials according to claim 7 where the material that traversed the drum lateral surfaces via the perforations is removed from the container by opening the container along a seam that separates connected portions and tilting at least one connected portion by rotation to pour out the material.

11. The process for treating materials according to claim 10 wherein the container is separated at a lateral seam to dispose a lower vessel under the drum that collects the material separated by the drum.

12. The process for treating materials according to claim 7 wherein the step of removing the drum from the container occurs after the step of orienting the drum with the base disposed above the opening to discharge material from the container.

* * * * *